(12) United States Patent
Lechmann et al.

(10) Patent No.: US 9,700,432 B2
(45) Date of Patent: *Jul. 11, 2017

(54) INTERVERTEBRAL PROSTHESIS OR DISK PROSTHESIS

(71) Applicant: DePuy Synthes Products, Inc., Raynham, MA (US)

(72) Inventors: Beat Lechmann, Grenchen (CH); Robert Frigg, Bettlach (CH); Roger Buerki, Balsthal (CH)

(73) Assignee: DePuy Synthes Products, Inc., Raynham, MA (US)

( * ) Notice: Subject to any disclaimer, the term of this patent is extended or adjusted under 35 U.S.C. 154(b) by 59 days.

This patent is subject to a terminal disclaimer.

(21) Appl. No.: 14/638,196

(22) Filed: Mar. 4, 2015

(65) Prior Publication Data
US 2015/0173913 A1 Jun. 25, 2015

Related U.S. Application Data

(63) Continuation of application No. 11/587,723, filed as application No. PCT/CH2004/000250 on Apr. 26, 2004, now Pat. No. 8,992,618.

(51) Int. Cl.
*A61F 2/44* (2006.01)
*A61F 2/30* (2006.01)
*A61F 2/46* (2006.01)

(52) U.S. Cl.
CPC .............. *A61F 2/447* (2013.01); *A61F 2/441* (2013.01); *A61F 2/442* (2013.01); *A61F 2/446* (2013.01);

(Continued)

(58) Field of Classification Search
CPC ............ A61F 2/4455; A61F 2002/4475; A61F 2002/2835; A61F 2002/30785
See application file for complete search history.

(56) References Cited

U.S. PATENT DOCUMENTS 4,338,925 A 7/1982 Miller
4,405,249 A 9/1983 Scales
(Continued)

FOREIGN PATENT DOCUMENTS

DE 197 10 392 C1 7/1999
FR 2 820 630 A1 8/2002
(Continued)

OTHER PUBLICATIONS

International Search Report for Application No. PCT/CH2004/000250 issued Dec. 28, 2004 (6 pages).
(Continued)

*Primary Examiner* — Lynnsy Summitt
(74) *Attorney, Agent, or Firm* — Nutter McClennen & Fish LLP (57) ABSTRACT

An intervertebral prosthesis or disk prosthesis comprising a front side, a rear side, an upper side which can be placed on the base plate of vertebral body, a lower side which can be placed on the base plate of a vertebral body, a right side, a left side, a cavity which can receive a fluid hydraulic osteocementum, an opening in the cavity and several outlets out from the cavity. The total of the transversal surfaces of the outlets $S_V$ on the front side, the total of the transversal surfaces of the outlets $S_H$ on the rear side, the total of the transversal surfaces of the outlets $S_R$ on the right side and the total of the transversal surfaces of the outlets on the left side satisfy the following conditions: $S_L > S_R$ or $S_R > S_L$ or $S_H > S_V$ or $S_V > S_H$.

18 Claims, 7 Drawing Sheets

(52) U.S. Cl.
CPC ............... *A61F 2002/30777* (2013.01); *A61F 2002/30785* (2013.01); *A61F 2002/30789* (2013.01); *A61F 2002/30841* (2013.01); *A61F 2002/448* (2013.01); *A61F 2002/4475* (2013.01); *A61F 2002/4631* (2013.01); *A61F 2310/00353* (2013.01)

(56) References Cited

U.S. PATENT DOCUMENTS

| | | | |
|---|---|---|---|
| 4,736,738 | A | 4/1988 | Lipovsek et al. |
| 4,863,476 | A | 9/1989 | Shepperd |
| 5,123,926 | A | 6/1992 | Pisharodi |
| 5,214,987 | A | 6/1993 | Fenton, Sr. |
| 5,397,364 | A | 3/1995 | Kozak et al. |
| 5,571,189 | A | 11/1996 | Kuslich |
| 5,665,122 | A | 9/1997 | Kambin |
| 5,669,909 | A * | 9/1997 | Zdeblick ............ A61B 17/1671 606/247 |
| 5,697,932 | A | 12/1997 | Smith et al. |
| 5,888,224 | A * | 3/1999 | Beckers ............... A61F 2/4455 623/17.16 |
| 6,039,761 | A | 3/2000 | Li et al. |
| 6,048,343 | A | 4/2000 | Mathis et al. |
| 6,059,829 | A | 5/2000 | Schlapfer et al. |
| 6,110,179 | A | 8/2000 | Flivik et al. |
| 6,123,705 | A | 9/2000 | Michelson |
| 6,176,882 | B1 | 1/2001 | Biedermann et al. |
| 6,485,517 | B1 | 11/2002 | Michelson |
| 6,645,213 | B2 | 11/2003 | Sand et al. |
| 6,676,664 | B1 | 1/2004 | Al-Assir |
| 6,726,722 | B2 | 4/2004 | Walkenhorst et al. |
| 6,733,535 | B2 | 5/2004 | Michelson |
| 6,923,810 | B1 | 8/2005 | Michelson |
| 6,953,477 | B2 | 10/2005 | Berry |
| 7,128,760 | B2 * | 10/2006 | Michelson ............... A61F 2/446 606/247 |
| 7,156,877 | B2 | 1/2007 | Lotz et al. |
| 7,316,689 | B2 | 1/2008 | Lieberman |
| 7,361,193 | B2 * | 4/2008 | Frey ........................ A61B 17/58 623/17.11 |
| 7,500,991 | B2 * | 3/2009 | Bartish, Jr. ............ A61F 2/4611 623/17.11 |
| 7,591,852 | B2 * | 9/2009 | Prosser ................. A61F 2/4465 623/17.11 |
| 7,637,954 | B2 | 12/2009 | Michelson |
| 7,655,027 | B2 | 2/2010 | Michelson |
| 7,703,727 | B2 | 4/2010 | Selness |
| 7,731,751 | B2 | 6/2010 | Butler et al. |
| 7,799,081 | B2 | 9/2010 | McKinley |
| 7,837,734 | B2 | 11/2010 | Zucherman et al. |
| 7,850,733 | B2 | 12/2010 | Baynham et al. |
| 8,002,833 | B2 | 8/2011 | Fabris Monterumici et al. |
| 8,105,382 | B2 | 1/2012 | Olmos et al. |
| 8,262,666 | B2 | 9/2012 | Baynham et al. |
| 8,267,939 | B2 | 9/2012 | Cipoletti et al. |
| 8,343,193 | B2 | 1/2013 | Johnson et al. |
| 8,366,777 | B2 | 2/2013 | Matthis et al. |
| 8,992,618 | B2 * | 3/2015 | Lechmann .............. A61F 2/447 606/94 |
| 9,408,719 | B2 | 8/2016 | Lechmann et al. |
| 2001/0005796 | A1 | 6/2001 | Zdeblick et al. |
| 2001/0032018 | A1 | 10/2001 | Castro et al. |
| 2002/0029082 | A1 * | 3/2002 | Muhanna ............... A61F 2/4455 623/17.11 |
| 2002/0058947 | A1 | 5/2002 | Hochschuler et al. |
| 2002/0082700 | A1 | 6/2002 | Bianchi et al. |
| 2002/0092871 | A1 | 7/2002 | Rickard et al. |
| 2002/0147497 | A1 | 10/2002 | Belef et al. |
| 2003/0036762 | A1 | 2/2003 | Kerr et al. |
| 2003/0100950 | A1 | 5/2003 | Moret |
| 2004/0010260 | A1 | 1/2004 | Scribner et al. |
| 2004/0030389 | A1 | 2/2004 | Ferree |
| 2004/0127993 | A1 * | 7/2004 | Kast ........................ A61F 2/447 623/17.16 |
| 2004/0186572 | A1 | 9/2004 | Lange et al. |
| 2005/0038513 | A1 | 2/2005 | Michelson |
| 2005/0070900 | A1 * | 3/2005 | Serhan ............... A61B 17/3468 623/17.12 |
| 2005/0119747 | A1 * | 6/2005 | Fabris Monterumici ....... A61B 17/025 623/17.11 |
| 2005/0149192 | A1 | 7/2005 | Zuckerman et al. |
| 2005/0261781 | A1 | 11/2005 | Sennett et al. |
| 2006/0058878 | A1 * | 3/2006 | Michelson .............. A61F 2/446 623/17.11 |
| 2006/0122701 | A1 | 6/2006 | Kiester |
| 2007/0161962 | A1 | 7/2007 | Edie et al. |
| 2008/0071284 | A1 | 3/2008 | Lechmann et al. |
| 2008/0133015 | A1 | 6/2008 | Lechmann et al. |
| 2015/0223943 | A1 | 8/2015 | Lechmann et al. |

FOREIGN PATENT DOCUMENTS

| | | |
|---|---|---|
| FR | 2 836 373 A1 | 8/2003 |
| WO | 97/23174 A1 | 7/1997 |
| WO | 97/37619 A1 | 10/1997 |
| WO | 00/74605 A1 | 12/2000 |
| WO | 01/56513 A1 | 8/2001 |
| WO | 02/078514 A2 | 10/2002 |
| WO | 03/71992 A2 | 9/2003 |

OTHER PUBLICATIONS

International Preliminary Report on Patentability for Application No. PCT/CH2004/000250 issued Jun. 29, 2006 (14 pages).

U.S. Appl. No. 11/587,722—Non Final Office Action Dated Jun. 23, 2009.

U.S. Appl. No. 11/587,722—Amendment in Response to Non Final Office Action.

U.S. Appl. No. 11/587,722—Final Office Action Dated Jan. 25, 2010.

European Office Action for Application No. 04729392.3, issued Mar. 28, 2017 (7 pages).

* cited by examiner

INTERVERTEBRAL PROSTHESIS OR DISK PROSTHESIS

CROSS-REFERENCE TO RELATED APPLICATIONS

This application is a continuation of U.S. application Ser. No. 11/587,723, filed on Sep. 4, 2007, which is a national stage entry pursuant to 35 U.S.C. §371 of International Application No. PCT/CH04/00250. Each of the above applications is hereby incorporated herein by reference in its entirety.

FIELD

The invention relates to an intervertebral prosthesis or disk prosthesis, especially for arthrodesis surgery by means of dorsal access PLIF (posterior lumbar interbody fusion), TLIF (transforaminal lumbar interbody fusion), ELIF (extra-foraminal lumbar interbody fusion), ALIF (anterior lumbar interbody fusion) and ACIF (anterior cervical interbody fusion. The objective of this surgical technique is the treatment of a degenerated or otherwise diseased intervertebral disk. The surgeon looks for access to the intervertebral disk through a centrally placed skin incision. Subsequently, he exposes the rear region of the movement segments, especially the laminae and the pedicle entry points. By means of a partial resection of the facettal and laminar components, the surgeon aims past the nerve roots and the medullary space in the direction of the diseased intervertebral disk.

BACKGROUND

For this surgical technique, only a limited amount of autologous spongiosa is available for filling the cavities of cage-like intervertebral or disk prosthesis and the spaces between individual implants and their surroundings. In the long term, the arthrodesis takes place not with the implant but between the bone and the bone replacement material. The individual implants therefore function only as place holders or spacers.

The intervertebral spaces, supplied with the known intervertebral implants, therefore frequently do not attain complete arthrodesis, that is, they end in a pseudoarthrosis. The situation is much the same also with cage-like intervertebral implants for the cervical spine, as well as for those, which were inserted through ventral entrances. Such intervertebral spaces are not stable mechanically, as would have been expected from a stiffening. The consequences then may be recurring pain with subsequent revision surgery.

For the implants and surgical techniques described above, the surgeon uses autologous bone material, which he obtains from the resected parts of the vertebral body or by means of an additional intervention in the crest of the ilium. Since dorsal accesses to the intervertebral disk space are very narrow, the applying of bone material is made difficult. The surgeon is unable to ensure that the whole of the intervertebral space is filled with autologous bone material. There is therefore the danger that empty spaces will result which, on the one hand, permits migration of the implant. On the other hand, the spaces, not filled with autologous bone material, are filled by a soft, fibrous tissue.

SUMMARY

It is an object of the invention to provide an intervertebral prosthesis or a disk prosthesis, which makes an asymmetric emergence of the osteocementum possible, so that individual regions between the vertebral bodies (for example the central and posteriors zones) are automatically supplied with more osteocementum than other regions.

This objective is accomplished by an intervertebral prosthesis or disc prosthesis, for which the outlet openings are dimensioned differently in size. The amount of osteocementum $K_L$, emerging through $S_L$ is either larger or smaller than the amount of osteocementum $K_R$ emerging through $S_R$; or the amount of osteocementum $K_H$, emerging through $S_H$, is larger or smaller than the amount of osteocementum $K_V$ emerging through $S_V$.

In other words, the outlet openings are dimensioned so that, when flowable osteocementum is supplied through the inlet opening into the cavity, the amount of osteocementum $K_L$ emerging through $S_L$ is either larger or smaller than the amount of osteocementum $K_R$ emerging through $S_R$ or the amount of osteocementum $K_H$, emerging through $S_H$, is larger or smaller than the amount of osteocementum $K_V$, emerging through $S_V$.

The invention permits the intervertebral space to be filled with synthetic bone material (osteocementum) after the cage-like intervertebral prosthesis or disk prosthesis has been placed. The implant is secured by the emergence and subsequent curing of the flowable, hydraulic osteocementum. Due to the asymmetric arrangement of the outlet openings in the implant, the osteocementum can be spread selectively. The inventive prosthesis furthermore has the advantage that it makes superfluous the additional removal of bone at the crest of the iliac, which can cause long enduring pain.

In a special embodiment, the inlet opening is provided in the front side of the prosthesis and the cavity extends from the inlet opening in the direction of the rear side.

In the case of a further embodiment, the inlet opening is disposed in the left all right side of the prosthesis and the cavity extends from the inlet opening in the direction of the opposite right or left side.

In the case of a further embodiment, the cross section of the cavity decreases at least on a partial section as the distance from the inlet opening increases. Due to the tapering of the cavity, the liquid cement mixture flows more easily through the side openings of the implant. The wall of the implant in the opening opposite the injection point has a shearing-off edge, so that the liquid cement mixture is diverted.

In the case of a further embodiment, the cavity tapers, at least on a partial section, either in wedge-shaped or conical fashion. In the case of a further embodiment, the upper and lower sides converge in the direction of the front side at least on a partial section. In yet another embodiment, the prosthesis is filled at least partially with a cured hydraulic osteocementum, which extends at least partially beyond the outlet opening.

In the case of a further embodiment, the implant may consist of two intervertebral prostheses, which are disposed next to one another, the right side of the intervertebral prosthesis disposed on the left being oriented in the direction of the left side of the intervertebral prosthesis disposed on the right. For the intervertebral prosthesis disposed on the left, the condition $S_L > S_R$ applies and for the intervertebral prosthesis on the right, the condition $S_R > S_L$.

Moreover, the intervertebral prosthesis may be varied in many ways, for example, by using flat, concave, convex or also spherical side walls.

Calcium phosphate cements, which, after the two components are mixed, may be injected in liquid form into the implant and are subsequently cured hydraulically, are suitable as flowable hydraulic osteocementum.

BRIEF DESCRIPTION OF THE DRAWINGS

The invention and further development of the invention are described in even greater detail by means of several examples and partially diagrammatic drawings, in which.

DETAILED DESCRIPTION OF THE PREFERRED EMBODIMENTS

Figure 1:
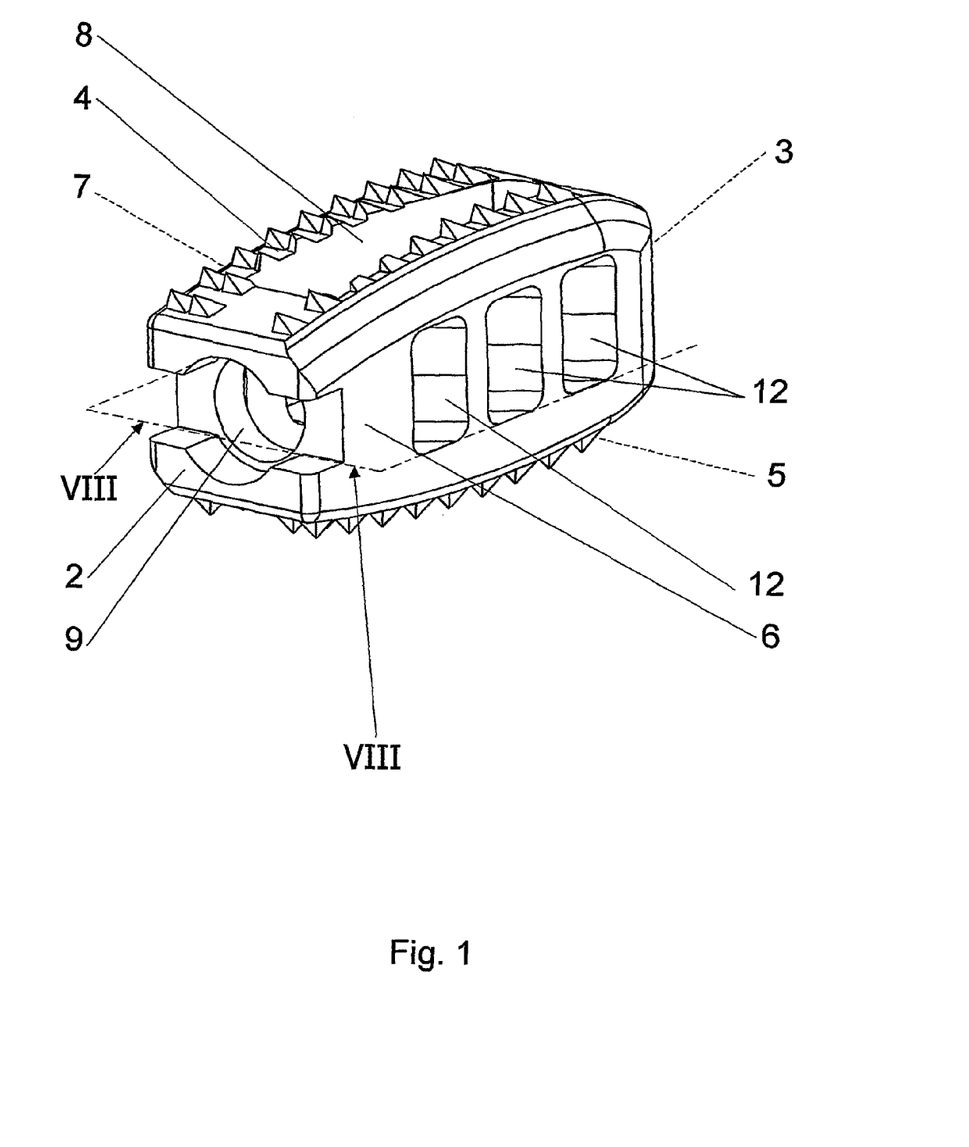
FIG. 1 shows a perspective view of an inventive, lens-shaped intervertebral implant.
Figure 2:
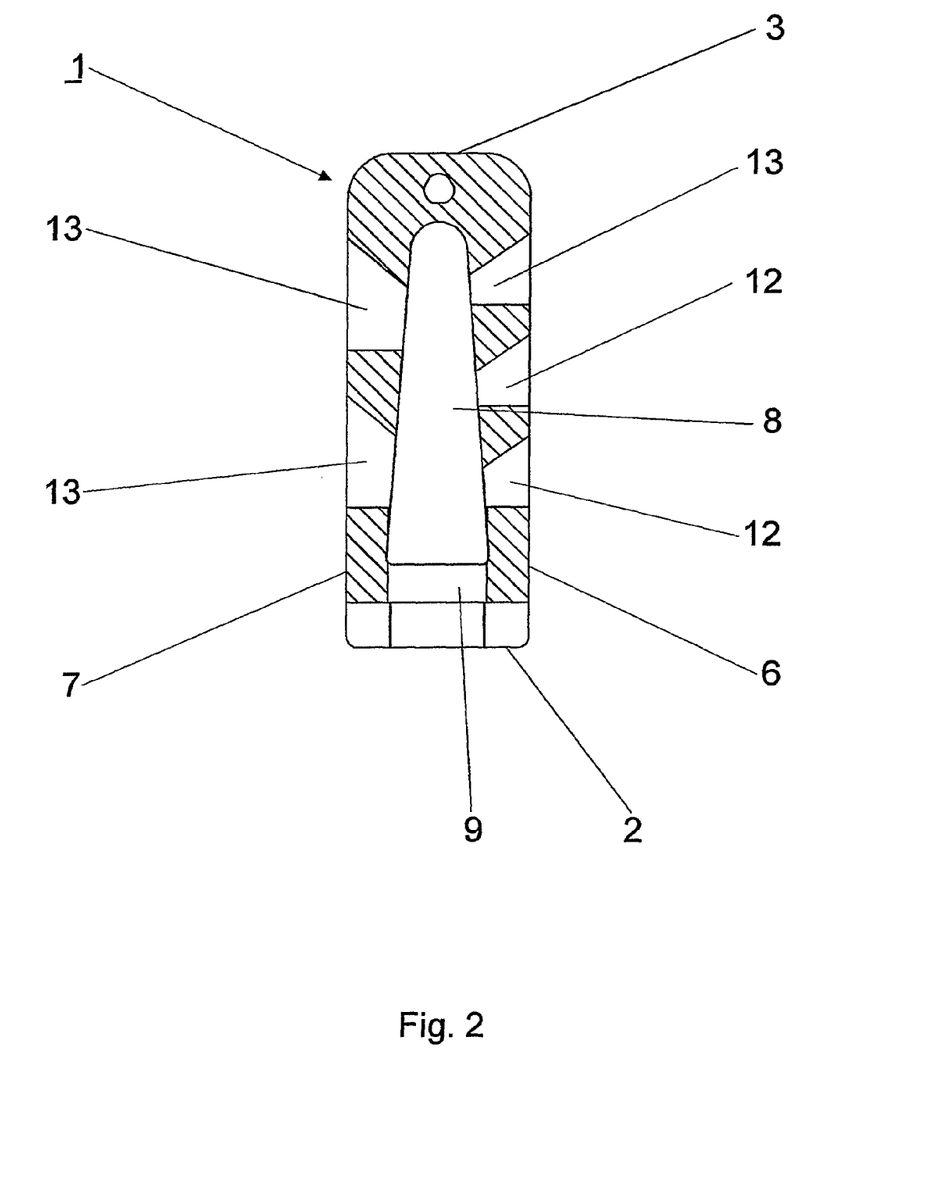
FIG. 2 shows a longitudinal section through the intervertebral implant of FIG. 1 along the central plane VIII-VIII.

The intervertebral prosthesis 1, shown in FIGS. 1 and 2, consists of a rectangular hollow body and has a front side 2, a rear side 3, an upper side 4 suitable for positioning against the baseplate of a vertebral body, a lower side 5 suitable for positioning against the baseplate of a vertebral body, a right side 6, a left side 7, a cavity 8 suitable for accommodating a flowable, hydraulic osteocementum, an inlet opening 9 into the cavity 8 and several outlet openings 10; 11; 12; 13 from the cavity 8. The upper side 4 and the lower side 5 converge toward the front side 2 as well as toward the rear side 3, so that a lens-like configuration of the intervertebral prosthesis results.

As can be seen from FIG. 2, the cross section of the cavity 8 decreases in the shape of a cone as the distance from the inlet opening 9 increases.

Figure 3:
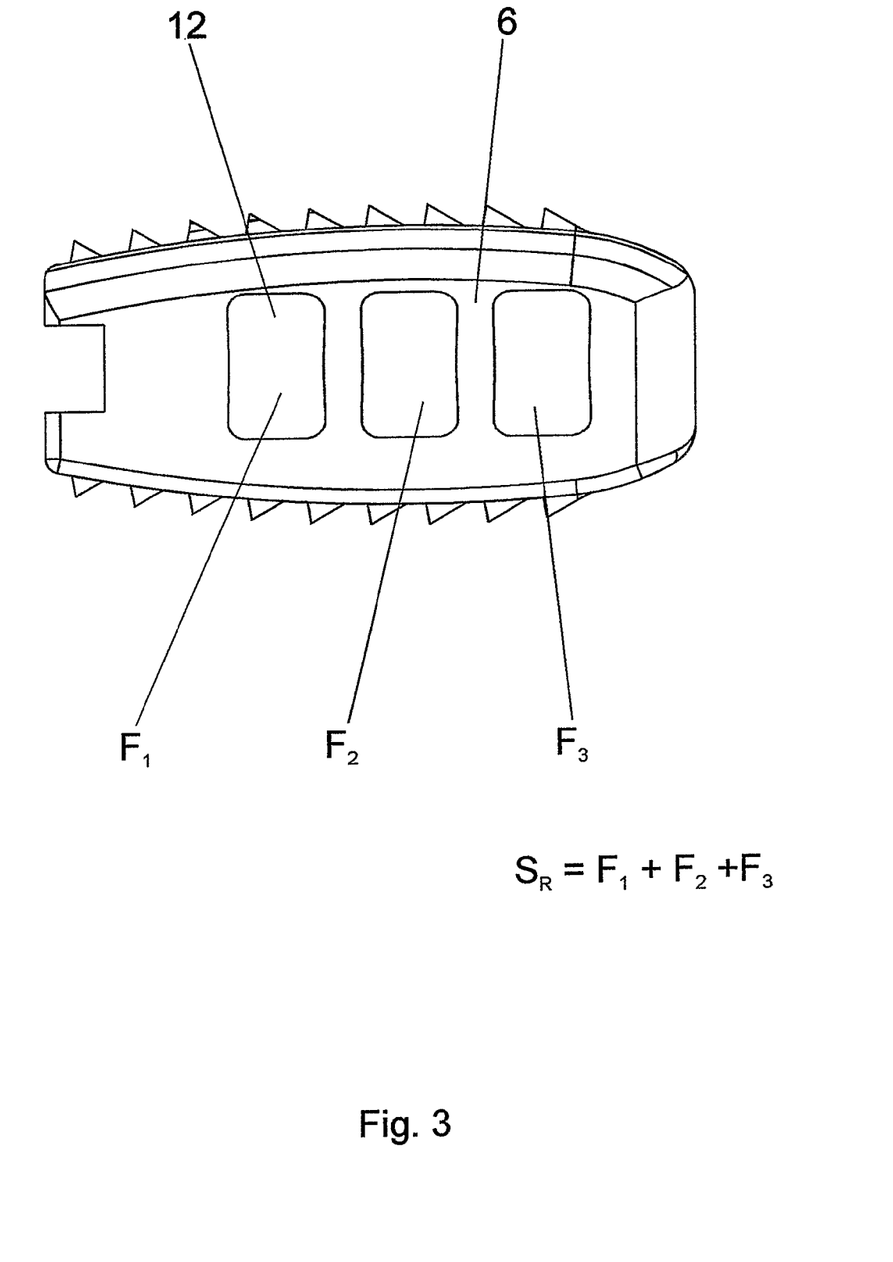
FIG. 3 shows a side view from the right of the intervertebral implant of FIG. 1.

As shown in FIG. 3, there are three outlet openings 12 with areas $F_1$, $F_2$ and $F_3$ in the right side 6 of the intervertebral prosthesis 1, so that the sum $S_R$ of the cross sectional surfaces of the outlet openings emerging the right side 6 is $S_R = F_1 + F_2 + F_3$.

Figure 4:
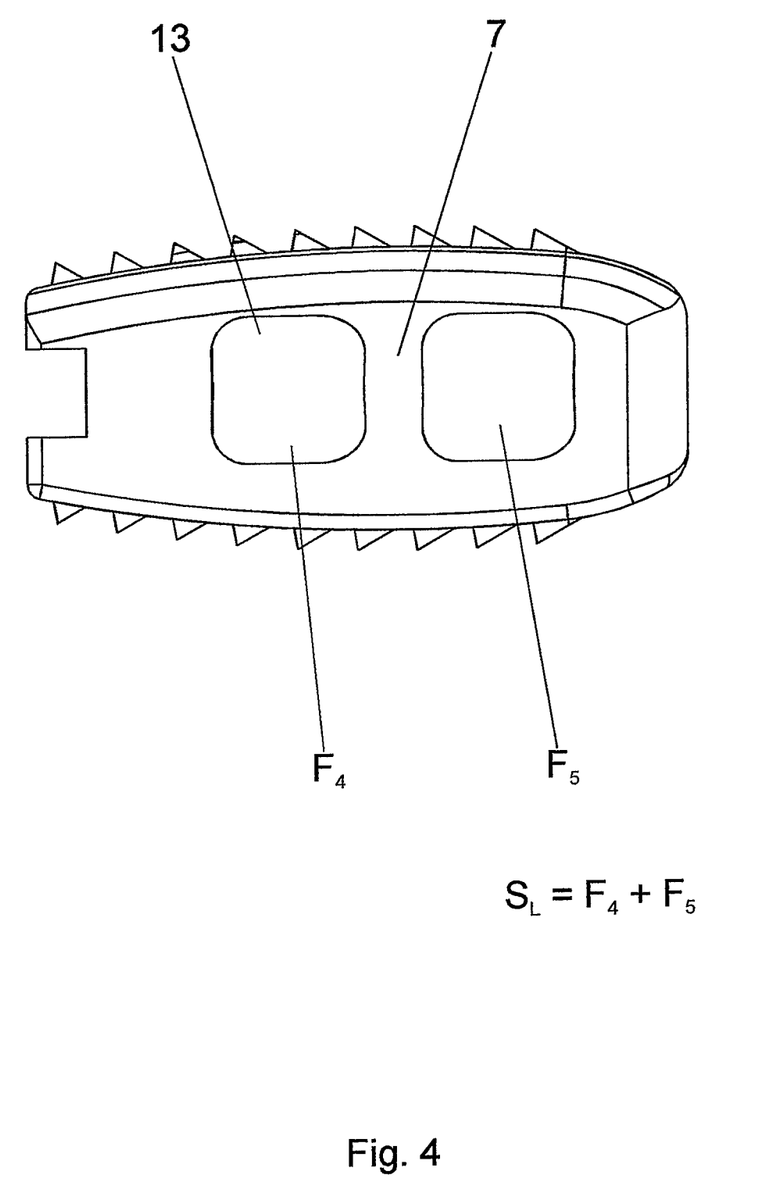
FIG. 4 shows a side view from the left of the intervertebral implant of FIG. 1.

As shown in FIG. 4, there are two outlet openings 13 with the areas $F_4$ and $F_5$ in the left side 7 of the intervertebral prosthesis 1, so that the sum $S_L$ of the cross-sectional surfaces of the outlet openings emerging for the left side 7 is $S_L = F_4 + F_5$.

It is important that the sum $S_L > S_R$, so that more osteocementum can emerge on the left side 7 of the intervertebral prosthesis 1 from the cavity 8 through the outlet opening 13 into the intervertebral space than from the right side 6.

Figure 5:
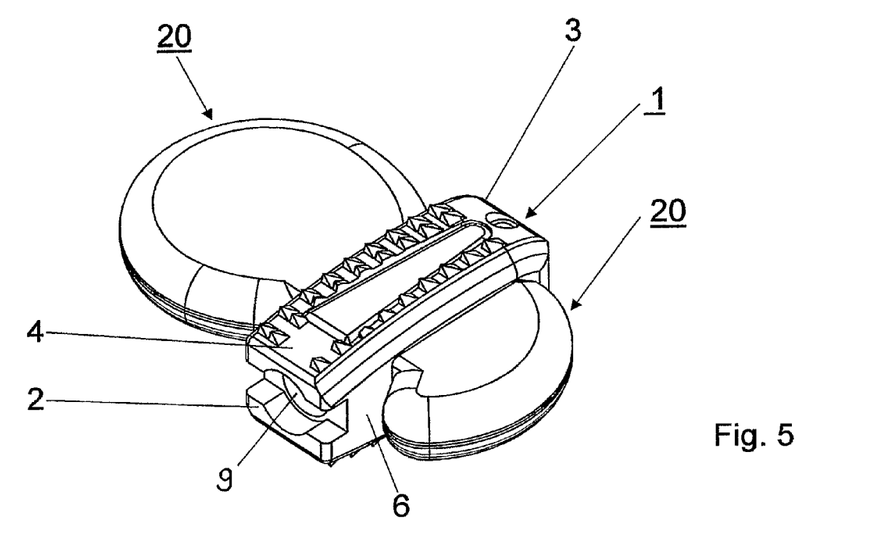
FIG. 5 shows a perspective view of an inventive intervertebral prosthesis, which is secured by means of cured osteocementum.
Figure 6:
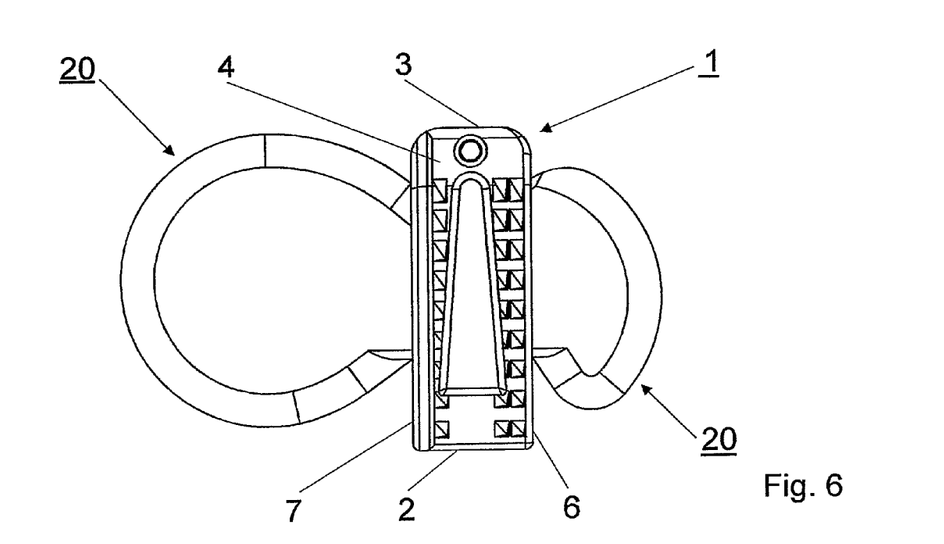
FIG. 6 shows a plan view of the intervertebral prosthesis of FIG. 5.

FIGS. 5 and 6 show how the osteocementum 20, emerging from the right side 6 and the left side 7 of the intervertebral prosthesis 1, is distributed. Because the sum $S_L$ of the cross sectional areas of the outlet openings 13 emerging on the left side 7 is larger, the amount of osteocementum 20, emerging on the left side 7 and curing, is also larger than that emerging on the right side 6 and curing.

Figure 7:
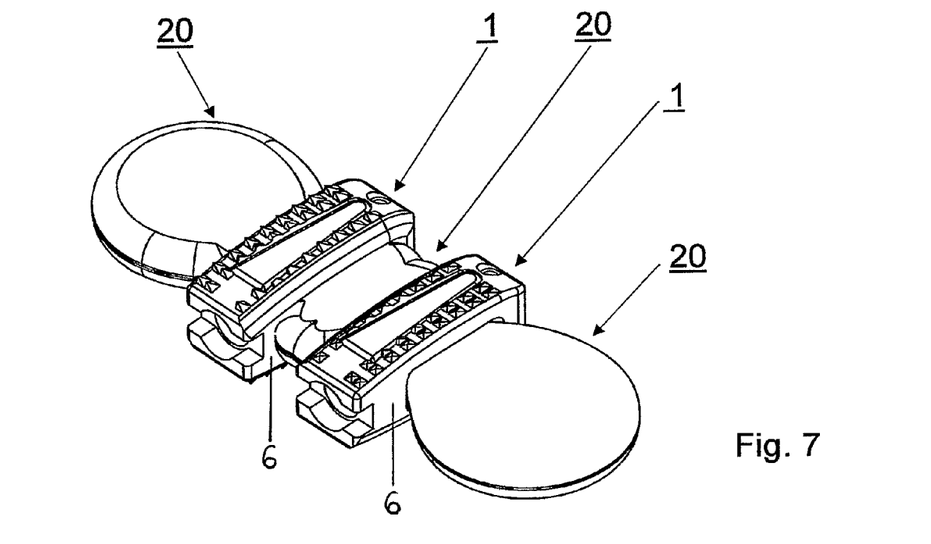
FIG. 7 shows a perspective view of a variation of the embodiment, using two intervertebral implants, the osteocementum securing the implant in their position relative to one another as well as to prevent migrating apart.
Figure 8:
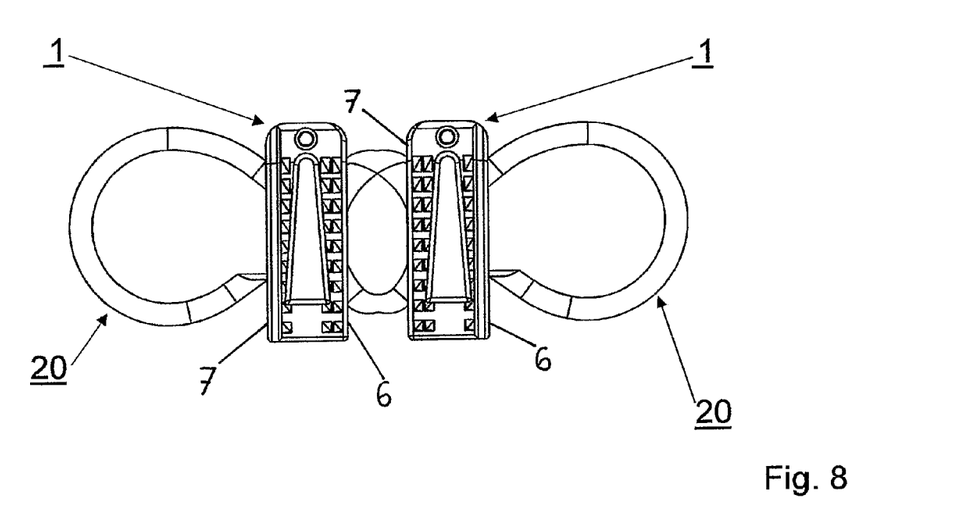
FIG. 8 shows a plan view of the two intervertebral implants of FIG. 7.

FIGS. 7 and 8 show a further embodiment, which consists of two inventive intervertebral prosthesis 1, which are disposed next to one another. The two intervertebral prostheses are positioned in such a manner, that the right side 6 of the intervertebral prosthesis 1, which is disposed on the left, is oriented in the direction of the left side 7 of the intervertebral prosthesis 1, which is disposed on the right. For the intervertebral prosthesis 1, disposed on the left, the condition $S_L > S_R$ applies, whereas, for the intervertebral prosthesis 1, which is disposed on the right, the reverse applies, namely $S_R > S_L$. Due to this measure, less osteocementum 20 emerges in the space between the two intervertebral prostheses 1 than emerges to the right side of the intervertebral prosthesis 1 disposed on the right and to the left side 7 of the intervertebral prosthesis 1 disposed on the left.

Figure 9:
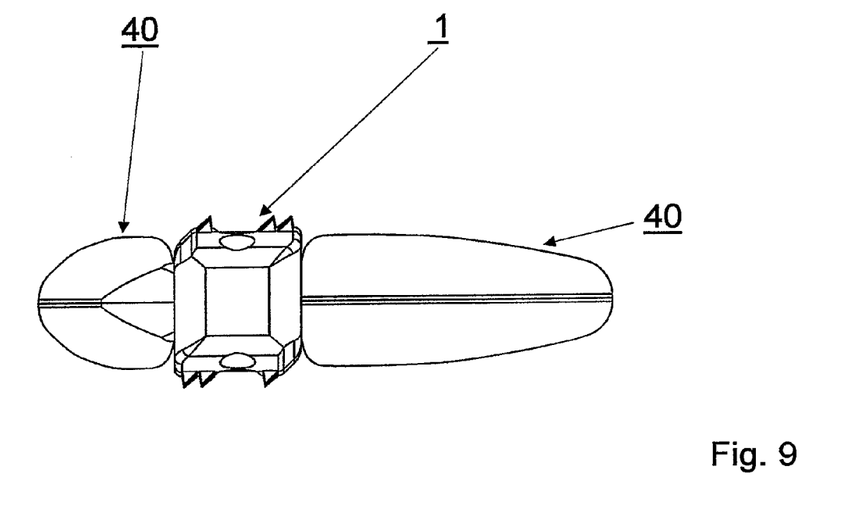
FIG. 9 shows a front view of a variation of the embodiments, in which the perforated intervertebral implant has a rectangular cross section

FIG. 9 shows a variation of the embodiment of an inventive intervertebral implant 1, which has a rectangular cross section and from which a larger amount of osteocementum 40 has emerged on the right side than on the left side.

Figure 10:
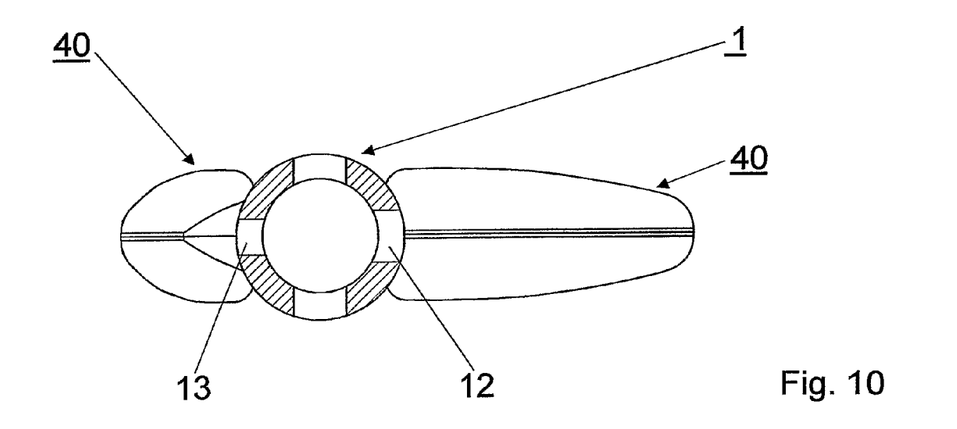
FIG. 10 shows a front view of a variation of the embodiment, in which the perforated intervertebral implant has a circular ring-shaped cross section.

FIG. 10 shows a further variation of an embodiment of an intervertebral prosthesis 1, which has a circular cross section and for which the amount of osteocementum 40 emerging on the right side through the outlet openings 12 is larger than that emerging on the left side through outlet openings 13.

The invention claimed is:

1. An intervertebral implant assembly, comprising:
   an intervertebral implant for implantation between an upper vertebra and a lower vertebra;
   a volume of flowable material; and
   a delivery tool for conveying the flowable material to the intervertebral implant;
   wherein the implant includes:
      a cavity defined by a body having a first end for engaging the delivery tool, the first end having an inlet opening for receiving the flowable material;
      a top surface for contacting at least a portion of the upper vertebra;
      a bottom surface for contacting at least a portion of the lower vertebra;
      a second end opposite the first end;
      a first lateral side being substantially straight and having a first length extending between the first and second ends, a first height extending between the top and bottom surfaces, and at least one opening;
      a second lateral side being substantially straight and having a second length extending between the first and second ends, a second height extending between the top and bottom surfaces, and at least one opening, wherein the first length is substantially the same as the second length and the first height is substantially the same as the second height;
   wherein the implant is configured such that, when the implant is disposed in an intervertebral disc space, the flowable material flows asymmetrically out of the implant and into the surrounding disc space.

2. The assembly of claim 1, wherein:
   the at least one opening of the first lateral side has a combined cross-sectional area A1;

the at least one opening of the second lateral side has a combined cross-sectional area A2; and A1 is not equal to A2 thereby providing that the flowable material emerges asymmetrically from the implant through said openings.

3. The assembly of claim 2, wherein A1 is greater than A2 so that the volume of flowable material emerging through the first side is greater than the volume of flowable material emerging through the second side.

4. The assembly of claim 1, wherein the cavity extends from the inlet opening towards the second end.

5. The assembly of claim 1, wherein the implant has a rectangular cross section.

6. The assembly of claim 1, wherein a cross-sectional area of the cavity decreases as the distance from the inlet opening increases.

7. The assembly of claim 1, wherein a cross-sectional area of the cavity decreases in one of a wedge-shape or a conical shape.

8. The assembly of claim 1, wherein the top surface and the bottom surface converge towards the second end.

9. The assembly of claim 1, wherein the flowable material comprises osteocementum.

10. An intervertebral implant assembly, comprising:
an implantable intervertebral cage configured for placement between an upper vertebra and a lower vertebra; and
a delivery tool configured to deliver flowable material to a cavity of the cage;
wherein the cage includes:
a first end for engaging the delivery tool, the first end having an inlet opening for receiving flowable material;
a second end opposite the first end, the second end being closed so that flowable material cannot emerge therefrom;
a top surface for contacting at least a portion of the upper vertebra;
a bottom surface for contacting at least a portion of the lower vertebra;
first and second substantially straight sidewalls having equal lengths and having at least one opening formed therein through which flowable material can emerge from the cage;
wherein the implant is configured such that, when the implant is disposed in an intervertebral disc space, flowable material delivered to the cavity flows asymmetrically out of the implant and into the surrounding disc space.

11. An intervertebral implant assembly, comprising:
an implantable intervertebral cage configured for placement between an upper vertebra and a lower vertebra; and
a delivery tool configured to deliver flowable material to a cavity of the cage;
wherein the cage includes:
a first end for engaging the deliver tool the first end having an inlet opening for receiving flowable material;
a second end opposite the first end, the second end being closed so that flowable material cannot emerge therefrom;
a top surface for contacting at least a portion of the upper vertebra;
a bottom surface for contacting at least a portion of the lower vertebra;
first and second substantially straight sidewalls having equal lengths and having at least one opening formed therein through which flowable material can emerge from the cage;
wherein the implant is configured such that, when the implant is disposed in an intervertebral disc space, a greater amount of flowable material emerges from the implant into a first lateral portion of the disc space than into a second lateral portion of the disc space opposite to the first lateral portion.

12. The assembly of claim 10, wherein:
the at least one opening of the first sidewall has a combined cross-sectional area A1;
the at least one opening of the second sidewall has a combined cross-sectional area A2; and
A1 is not equal to A2 thereby providing that the flowable material emerges asymmetrically from the implant.

13. The assembly of claim 12, wherein A1 is greater than A2 so that the volume of flowable material emerging through the first sidewall is greater than the volume of flowable material emerging through the second sidewall.

14. The assembly of claim 10, wherein the cavity extends from the inlet opening towards the second end.

15. The assembly of claim 10, wherein the implant has a rectangular cross section.

16. The assembly of claim 10, wherein a cross-sectional area of the cavity decreases as the distance from the inlet opening increases.

17. The assembly of claim 10, wherein a cross-sectional area of the cavity decreases in one of a wedge-shape or a conical shape.

18. The assembly of claim 10, wherein the flowable material comprises osteocementum.

* * * * *